(12) United States Patent
Duesdieker

(10) Patent No.: US 9,173,622 B2
(45) Date of Patent: Nov. 3, 2015

(54) ELEVATING AND ROTATING ULTRASOUND PATIENT STAND

(75) Inventor: Philomina Duesdieker, Salinas, CA (US)

(73) Assignee: Creative Ultrasound Imaging, Inc., Salinas, CA (US)

(*) Notice: Subject to any disclaimer, the term of this patent is extended or adjusted under 35 U.S.C. 154(b) by 755 days.

(21) Appl. No.: 13/288,857

(22) Filed: Nov. 3, 2011

(65) Prior Publication Data

US 2013/0111665 A1    May 9, 2013

(51) Int. Cl.
| | |
|---|---|
| A61B 6/04 | (2006.01) |
| A61G 13/12 | (2006.01) |
| A61B 5/055 | (2006.01) |
| A61B 5/00 | (2006.01) |
| A61B 8/00 | (2006.01) |

(52) U.S. Cl.
CPC ............. *A61B 6/0478* (2013.01); *A61B 5/0555* (2013.01); *A61B 5/70* (2013.01); *A61B 8/00* (2013.01); *A61G 13/12* (2013.01); *A61G 2210/50* (2013.01)

(58) Field of Classification Search
CPC ...... A61B 6/04; A61B 6/0421; A61B 6/0478; A61B 5/0555; A61B 5/70; A61B 8/00; A61B 8/40; A61G 2210/50; A61G 13/12
USPC ............... 5/11, 600, 601, 611, 612, 616–618, 5/621, 623, 635, 640, 646
See application file for complete search history.

(56) References Cited

U.S. PATENT DOCUMENTS

| | | | | |
|---|---|---|---|---|
| 1,442,027 | A * | 1/1923 | Levenson | 378/208 |
| 2,552,592 | A * | 5/1951 | Rush | 297/195.11 |
| 3,585,386 | A * | 6/1971 | Horton | 378/178 |
| 3,655,968 | A * | 4/1972 | Moore et al. | 378/178 |
| 3,851,644 | A * | 12/1974 | Slagle | 128/847 |
| 4,044,265 | A * | 8/1977 | Schmidt | 378/39 |
| 4,845,747 | A * | 7/1989 | Koike et al. | 378/208 |
| 4,896,917 | A * | 1/1990 | Enevoldson | 297/217.3 |
| 5,168,514 | A * | 12/1992 | Horton et al. | 378/209 |
| 5,250,019 | A * | 10/1993 | McGinley | 600/1 |
| 5,600,702 | A * | 2/1997 | Pigg | 378/180 |
| 5,933,887 | A * | 8/1999 | Strange et al. | 5/600 |
| 6,733,175 | B1 * | 5/2004 | Pigg | 378/167 |
| 7,634,057 | B2 * | 12/2009 | Ein-Gal | 378/69 |
| 7,796,730 | B2 * | 9/2010 | Marash et al. | 378/65 |
| 8,055,325 | B1 * | 11/2011 | Damadian et al. | 600/421 |
| 8,083,408 | B2 * | 12/2011 | Moyers | 378/205 |
| 8,218,723 | B2 * | 7/2012 | Ein-Gal | 378/37 |
| 2002/0014235 | A1 * | 2/2002 | Rogers et al. | 128/200.24 |
| 2008/0125641 | A1 * | 5/2008 | Jonas et al. | 600/415 |
| 2012/0324648 | A1 * | 12/2012 | Amano | 5/601 |

* cited by examiner

*Primary Examiner* — Nicholas Polito
*Assistant Examiner* — David R Hare
(74) *Attorney, Agent, or Firm* — LaRiviere, Grubman PC

(57) ABSTRACT

An elevating and rotating patient ultrasound stand facilitates accurate ultrasound evaluation. A base provides both elevation changes and rotation. An electric motor lifts and lowers the stand, and rotates on a "lazy susan" style base. One embodiment of a lifting mechanism is a scissors style mechanism and another embodiment is a hydraulic or pneumatic cylinder mechanism. The stand resides above the elevating and rotating mechanism and includes arm rests on each side. In one embodiment a seat is attachable to the stand to provide a patient with a rest from standing for a long period of time.

11 Claims, 4 Drawing Sheets

ELEVATING AND ROTATING ULTRASOUND PATIENT STAND

BACKGROUND OF THE INVENTION

The present invention relates to obtaining patient venous evaluation by ultrasound and in particular to an elevating and rotating stand facilitating ultrasound evaluation of a patient's lower extremity veins.

Ultrasound evaluation is often of a patients legs. Known methods for taking such evaluation includes several repositioning steps and require the ultrasound technologist to kneel or otherwise position themselves below the patient's waste. Thorough evaluation benefits from the ultrasound probe being positioned perpendicular to the skin and a very steady hold. Awkward positions often result making it difficult to achieve the best positioning, hampers obtaining accurate evaluation, and may cause damage to the ergonomic health of the technologist and the patient.

BRIEF SUMMARY OF THE INVENTION

The present invention addresses the above and other needs by providing an elevating and rotating patient ultrasound stand which facilitates accurate evaluation of venous hemodynamics. A base provides both elevation changes and rotation. An electric motor lifts and lowers the stand, and rotates on a "lazy susan" style base. One embodiment of a lifting mechanism is a scissors style mechanism and another embodiment is a hydraulic or pneumatic cylinder mechanism. The stand resides above the elevating and rotating mechanism and includes arm rests on each side and a seat to provide a patient with a rest from standing for a long period of time.

In accordance with one aspect of the invention, there is provided an elevating patient ultrasound stand. The height of the stand is controlled by electrical switches controlling an electrical drive. The height adjustment allows an ultrasound technologist to easily and accurately position an ultrasound probe for evaluation.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Figure 1C:
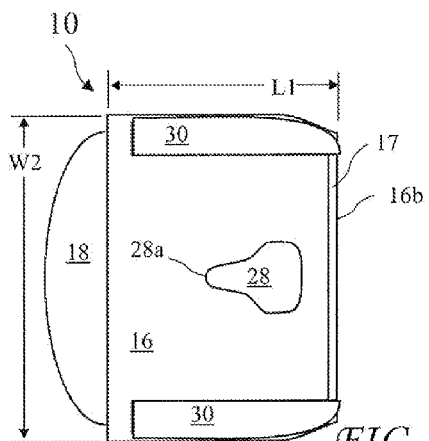
FIG. 1C is a top view of the elevating and rotating ultrasound patient stand according to the present invention.
Figure 1A:
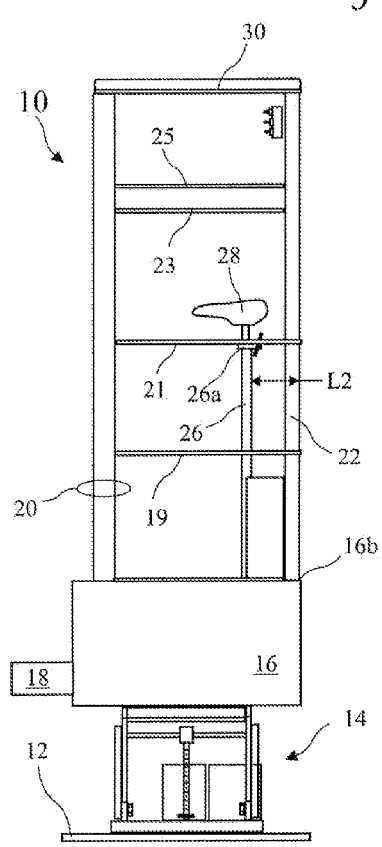
FIG. 1A is a side view of an elevating and rotating ultrasound patient stand according to the present invention.
Figure 1B:
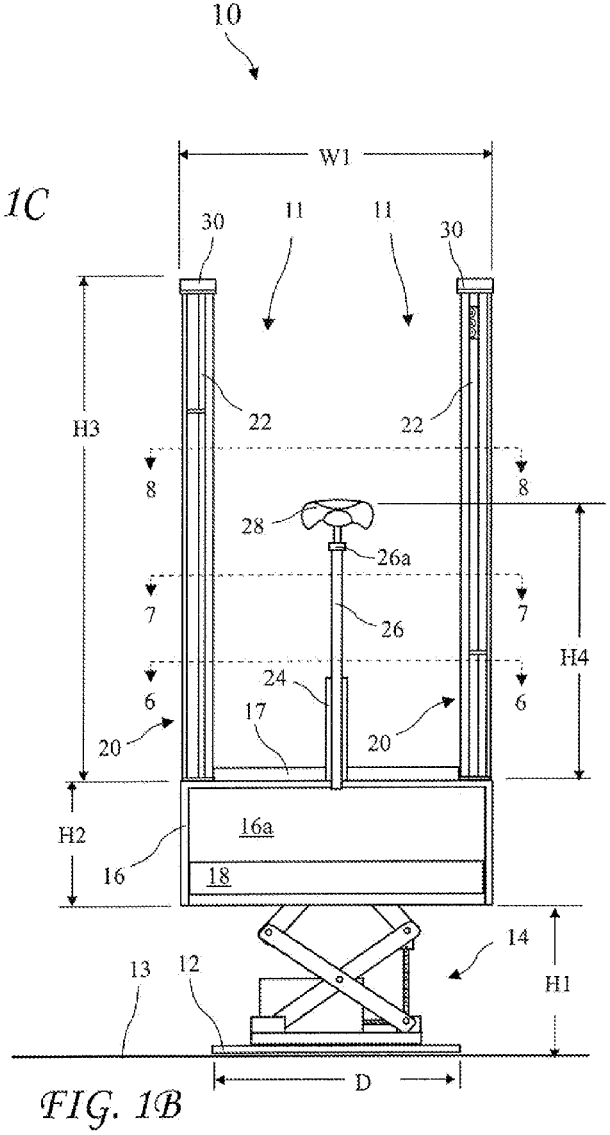
FIG. 1B is a front view of the elevating and rotating ultrasound patient stand according to the present invention.

A side view of an elevating and rotating ultrasound patient stand 10 according to the present invention is shown in FIG. 1A, a front view of the ultrasound patient stand 10 is shown in FIG. 1B, and a top view of the ultrasound patient stand 10 is shown in FIG. 1C. The ultrasound patient stand 10 includes a base 12 resting on a floor 13 or other horizontal surface. An elevation apparatus 14 is rotatably attached to the base 12, for example, but a lazy susan type apparatus. A platform 16 is attached to the elevation apparatus 14 and is preferably an open back 16a box like structure, the open back 16a providing a step for patients. A step extension 18 may extend to the front of the platform 16.

In one embodiment, a patient seat 28 may be provided to provide a patient with a rest from standing for a long period of time. The patient seat 28 may be supported by a vertical column (or tube) reaching up from the platform 16 and a bracing structure 24 may be fixed to the platform 16 at the base of the column 26. A seat height adjuster 26a may be attached proximal to the top of column 26 to allow adjustment of the seat height, for example, a bicycle style clamp. The patent seat 28 is preferably a bicycle style or triangular shaped seat. A nose 28a of the seat 28 points forward and the seat 28 is horizontally spaced away from a vertical plane which a rear edge 16b of the platform 16 resides in. The bicycle or triangular seat 28 allows free movement of patient legs.

Arm rests 30 are vertically supported from the platform 16 by horizontally spaced apart right and left arm rest supports. Preferable, each arm rest supports comprises a front vertical member 20 and a rear vertical member 22 supporting the arm rests 30. The front vertical members may comprise a pair of horizontally spaced apart vertical members 20a and 20b (see FIG. 6). First and second right horizontal members 19 and 21 connect the right vertical members 20 and 22. The first right horizontal member 19 is preferably a solid plate attached to the right vertical members 20, 22 about ¼ of the distance from the platform 16 to the right arm rest 30 and the second right horizontal member is preferably a pair of rods approximately aligned with ledges of the first right horizontal member 19 and connecting the right vertical members 20, 22 about midway between the platform 16 to the right arm rest 30. First and second left horizontal members 23 and 25 connect the left vertical members 20, 22. The first horizontal member 23 is preferably a solid plate attached to the right vertical members 20, 22 about ¾ of the distance from the platform 16 to the left arm rest 30 and the second horizontal member 25 is preferably a pair of rods approximately aligned with ledges of the first left horizontal member 23 and connecting the left vertical members 20, 22 about ¼ of way between first left horizontal member 23 and the left arm rest 30. Gaps 11 reside on each side of the seat 28.

The base 12 is preferably round with a diameter D of about 24 inches. The bottom of the platform 16 is a height H1 from the floor 13, which height H1 is raised and lowered by the elevating and rotating mechanism 14 providing a height adjustment of about thirteen inches for the platform 16 allowing the bottom of the platform 16 to the adjusted from a height of approximately twelve inches from the floor to a height of approximately 25 inches from the floor. The height H2 of the platform 16 is about 11 inches, and the height H3 from the top of the platform 16 to the arm rests 30 is about 43 inches. The seat 28 is height adjustable to reside a height H4 between 39 and 37 inches above the top of the platform 16. The platform 16 has a width W2 of about 31 inches and a length L1 of about 19.5 inches. The column 26 is spaced a length L2 of between six and fourteen inches and preferably about ten inches from the rear of the platform 16b. While these dimensions are preferred, those skilled in the art will recognize that the dimensions maybe varied and an ultrasound patient stand according top the present invention having altered dimensions is intended to come within the scope of the present invention.

Figure 2A:
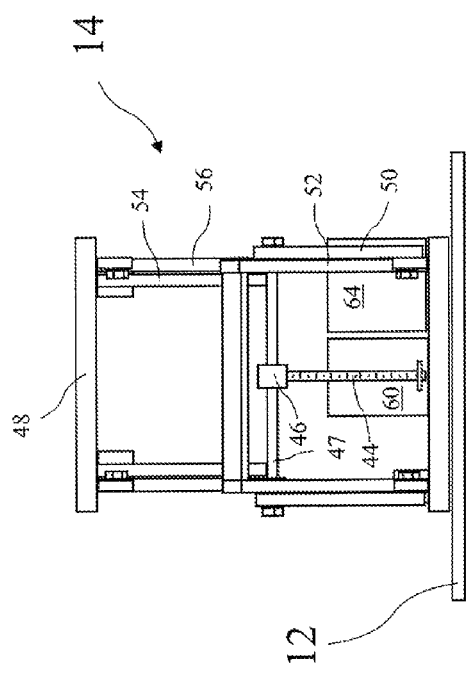
FIG. 2A is a detailed side view of a scissors type elevating and rotating mechanism of the elevating and rotating ultrasound patient stand according to the present invention in a raised position.
Figure 2B:
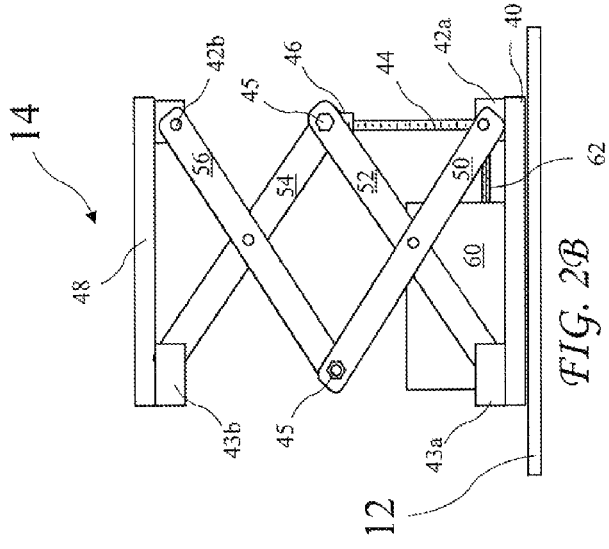
FIG. 2B is a detailed front view of the scissors type elevating and rotating mechanism according to the present invention in the raised position.
Figure 3A:
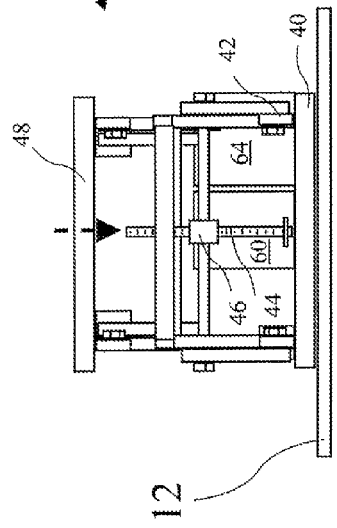
FIG. 3A is a detailed side view of the scissors type elevating and rotating mechanism according to the present invention in a lowered position.
Figure 3B:
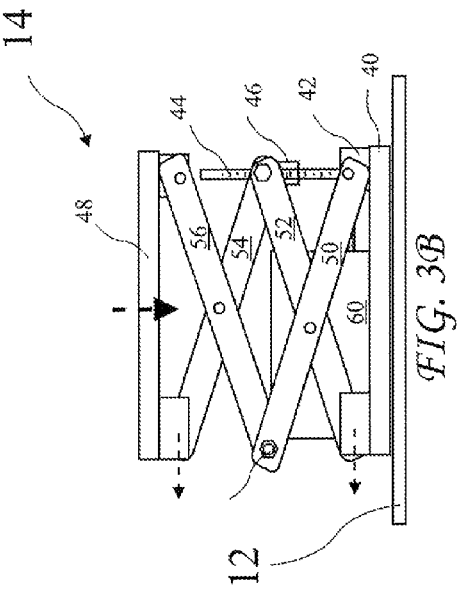
FIG. 3B is a detailed front view of the scissors type elevating and rotating mechanism according to the present invention in the lowered position.

A detailed side view of a scissors type elevating and rotating mechanism 14 according to the present invention is shown in a raised position in FIG. 2A, a detailed front view of the scissors type elevating and rotating mechanism 14 in the raise position is shown in FIG. 2B, a detailed side view of the scissors type elevating and rotating mechanism 14 is shown in a lowered position in FIG. 3A, and a detailed front view of the scissors type elevating and rotating mechanism 14 is shown in the lowered position in FIG. 3B. The scissors type elevating and rotating mechanism 14 is rotatably attached to the base 12 by a lower plate 40. The scissors type elevating and rotating mechanism 14 includes four pairs of links 50, 52, 54, and 56. The lower ends of the links 50 are pivotally attached to the lower plate 40 at pivots 42a and lower ends of the links 52 are slidably attached to the plate 40 at slides 43a. Upper ends of the links 50 are pivotally attached at pivots 45 to links 56 and upper ends of the links 52 are pivotally attached at pivots 45 to links 55. The upper ends of the links 56 are pivotally attached to the upper plate 40 at pivots 42b and upper ends of the links 54 are slidably attached to the plate 48 at slides 43b.

A screw 44 is threadedly attached to a cross bar 47 by a threaded collar 46. The screw 44 is rotated by a chain 62 driven by a motor 60. The screw 44 rotates but does not translate, thereby lifting and dropping the cross bar 47. The links 52 and 54 pivot about the axis of the cross bar 47 and lifting and dropping the cross bar 47 raises and lowers an upper plate 48 of the scissors type elevating and rotating mechanism 14, thereby raising and lowering the platform 16. A blower 64 resides under the platform 16 and provides a circulation of air.

Figure 4:
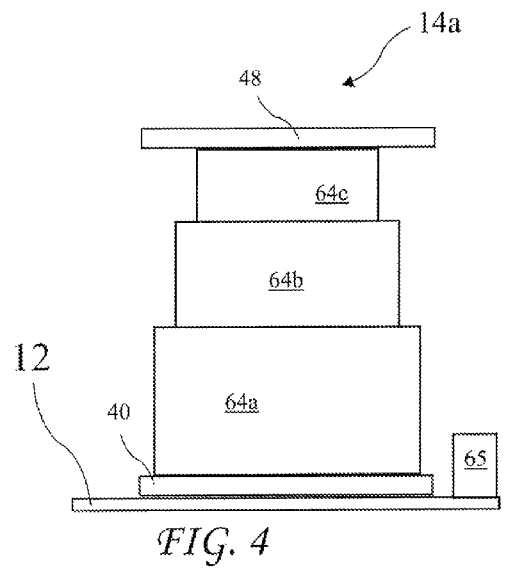
FIG. 4 is a detailed side view of a hydraulic or pneumatic type elevating and rotating mechanism of the elevating and rotating ultrasound patient stand according to the present invention in the raised position.
Figure 5:
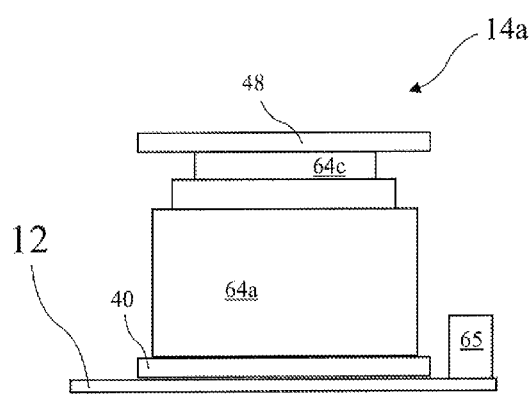
FIG. 5 is a detailed side view of a hydraulic or pneumatic type elevating and rotating mechanism according to the present invention in the lowered position.

A detailed side view of a hydraulic or pneumatic type elevating and rotating mechanism 14a of the elevating and rotating ultrasound patient stand 10 according to the present invention in the raised position in FIG. 4 and a detailed side view of a hydraulic or pneumatic type elevating and rotating mechanism 14a is shown in a lowered position in FIG. 5. A remote or attached pump 65 provides a pneumatic or hydraulic flow to raise the elevating and rotating ultrasound patient stand 10. The pump 65 is preferably an electric pump.

Figure 6:
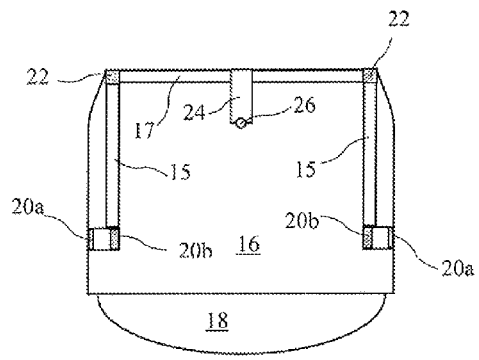
FIG. 6 is a cross-sectional view of the elevating and rotating ultrasound patient stand according to the present invention in the raised position taken along line 6-6 of FIG. 1B.
Figure 7:
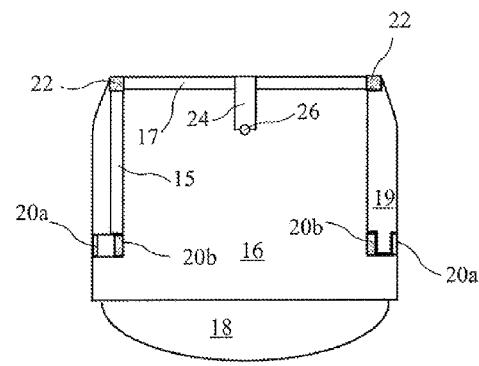
FIG. 7 is a cross-sectional view of the elevating and rotating ultrasound patient stand according to the present invention in the raised position taken along line 7-7 of FIG. 1B.
Figure 8:
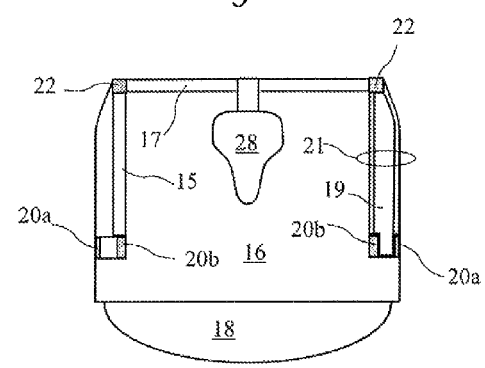
FIG. 8 is a cross-sectional view of the elevating and rotating ultrasound patient stand according to the present invention in the raised position taken along line 8-8 of FIG. 1B.

A cross-sectional view of the elevating and rotating ultrasound patient stand 10 taken along line 6-6 of FIG. 1B is shown in FIG. 6, a cross-sectional view of the elevating and rotating ultrasound patient stand 10 taken along line 7-7 of FIG. 1B is shown in FIG. 7, and a cross-sectional view of the elevating and rotating ultrasound patient stand 10 taken along line 8-8 of FIG. 1B is shown in FIG. 8. The bracing 15 and 17 residing on the top surface of the platform 16 braces the lower ends of the vertical supports 20 and 22. The first right horizontal member 19 connects the right vertical supports 20 and 22 providing additional bracing, and the second right horizontal support member 21 provides still more bracing for the right vertical supports 20 and 22. The horizontal support members 23 and 25 are similar to the horizontal members 19 and 21.

Figure 9:
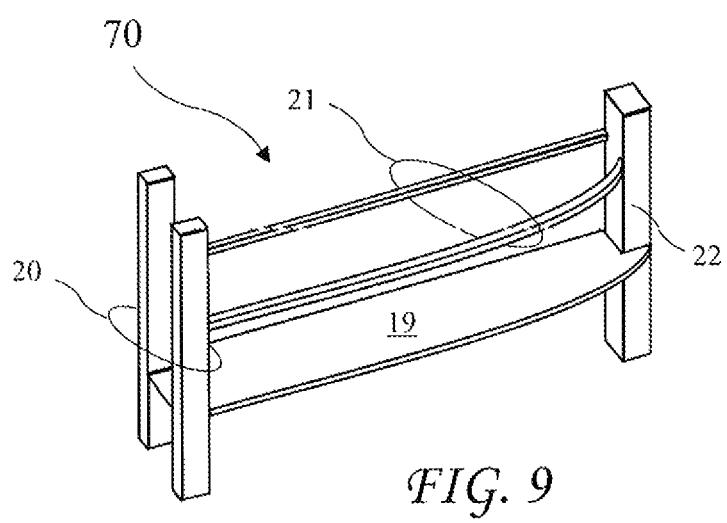
FIG. 9 is a shelf under a left arm rest according to the present invention.

A shelf 70 under the left arm rest 30 is shown in FIG. 9. The shelf 70 comprises the horizontal members 19 and 21. The horizontal member 19 provides a floor and the horizontal member 21 provide an upper edge for the shelf 70. A shelf 70 residing on the technologist's left when facing the patient (i.e., the patient's right) is higher and is for patient's use to place a water bottle or book etc. A shelf 70 on the technologist's right when facing the patient (i.e., the patient's left) is lower in position is for technologist's needs for the ultrasound coupling gel, clip board, towel and the like. In other embodiments the shelf may have solid sides, basket like sides, or the like, and an ultra sound patient stand having shelves of any form is intended to come within the scope of the present invention.

While the invention herein disclosed has been described by means of specific embodiments and applications thereof, numerous modifications and variations could be made thereto by those skilled in the art without departing from the scope of the invention set forth in the claims.

I claim:

1. An ultrasound patient stand comprising:
   an elevation apparatus rotatably mounted on a base;
   a platform mounted to the elevation apparatus, the elevation apparatus configured to raise and lower the platform;
   patient arm rests on left and right sides of a patient, wherein the arm rests are free standing and vertically supported by the platform;
   a patient seat vertically supported by the platform, wherein the patient seat is a triangular seat connected to the platform by a vertical support reaching from the platform to a bicycle style patient seat to position the triangular seat about ten inches forward of a rear edge of the platform, the triangular seat pointing towards the front of the platform to allow free movement of the patients legs; and
   the platform further having a step extension that reaches forward from the front of the platform.

2. The ultrasound patient stand of claim 1, wherein the patient seat is a bicycle style seat.

3. The ultrasound patient stand of claim 2, wherein the bicycle style patient seat is connected to the platform by a vertical support reaching from the platform to the bicycle style patient seat.

4. The ultrasound patient stand of claim 3, wherein the vertical support resided about ten inches forward from a rear edge of the platform to provide a patient with a rest from standing for a long period of time.

5. The ultrasound patient stand of claim 4, wherein a forward nose of the bicycle style seat is pointed away from the rear edge of the platform.

6. The ultrasound patient stand of claim 1, wherein horizontal gaps reside between the arm rests.

7. The ultrasound patient stand of claim 1, wherein the platform comprises a rectangular box having an open front providing a step for the patient.

8. The ultrasound patient stand of claim 1, wherein the elevation apparatus comprises a scissors apparatus.

9. The ultrasound patient stand of claim 1, wherein the elevation apparatus comprises a piston apparatus.

10. The ultrasound patient stand of claim 1, further including shelves attached on right and left sides of the stand residing between the platform and the arm rests, one shelf at a lower position for use by an ultrasound technologist and one shelf at a higher position for use by a patient.

11. The ultrasound patient stand of claim 1, further including a fan residing under the platform and providing circulation of air.

* * * * *